United States Patent [19]
Kleshinski

[11] Patent Number: 5,776,162
[45] Date of Patent: Jul. 7, 1998

[54] VESSEL IMPLANTABLE SHAPE MEMORY APPLIANCE WITH SUPERELASTIC HINGED JOINT

[75] Inventor: Stephen J. Kleshinski, Scituate, Mass.

[73] Assignee: Nitinol Medical Technologies, Inc., Boston, Mass.

[21] Appl. No.: 778,634

[22] Filed: Jan. 3, 1997

[51] Int. Cl.$^6$ .................................................. A61M 29/00
[52] U.S. Cl. .......................... 606/198; 606/191; 623/1; 623/12
[58] Field of Search .................................. 606/191, 195, 606/198, 200; 623/1, 12, 11

[56] References Cited

U.S. PATENT DOCUMENTS

| | | |
|---|---|---|
| 4,425,908 | 1/1984 | Simon . |
| 5,395,390 | 3/1995 | Simon et al. . |
| 5,545,210 | 8/1996 | Hess et al. ................................ 623/1 |
| 5,601,593 | 2/1997 | Freitag ................................ 606/198 |
| 5,702,419 | 12/1997 | Berry et al. ................................ 606/198 |

Primary Examiner—Michael Powell Buiz
Assistant Examiner—David O. Reip
Attorney, Agent, or Firm—Sixbey, Friedman, Leedom & Ferguson; Daniel W. Sixbey

[57] ABSTRACT

A medical appliance of shape memory material is provided for implantation in a vascular passageway for engagement with the walls of the passageway. The appliance includes a body formed of thermal shape memory material having a temperature transformation level below which the body is in a martensitic state and is pliable and compressible, and above which the body is in an austenitic state and is self-expandable to a substantially rigid pre-compressed configuration. The shape memory material in the austenitic state is capable of being transformed by stress to the martensitic state. The body includes segments which expand outwardly away from the longitudinal axis of the body in the austenitic state thereof, and a superelastic hinged joint is formed in at least one of the segments by reducing the cross-sectional area of the segment in a localized area.

16 Claims, 2 Drawing Sheets

VESSEL IMPLANTABLE SHAPE MEMORY APPLIANCE WITH SUPERELASTIC HINGED JOINT

BACKGROUND OF THE INVENTION

In recent years, a number of medical devices have been designed which are adapted for compression into a small size to facilitate introduction into a vascular passageway and which are subsequently expandable into contact with the walls of the passageway. These devices, among others, include stents for holding open a vascular passageway and blood clot filters which expand and are held in position by engagement with the inner wall of a vein. It has been found to be advantageous to form such devices of a shape memory material having a first, relatively pliable low temperature condition and a second, relatively rigid high-temperature condition. By forming such devices of temperature responsive material, the device in a flexible and reduced stress state may be compressed and fit within the bore of a delivery catheter when exposed to a temperature below a predetermined transition temperature, but at temperatures at or above the transition temperature, the device expands and becomes relatively rigid.

Known self expanding medical devices have been formed of Nitinol, an alloy of titanium and nickel which provides the device with a thermal memory. The unique characteristic of this alloy is its thermally triggered shape memory, which allows a device constructed of the alloy to be cooled below a temperature level and thereby softened for loading into a catheter in a relatively compressed and elongated state, and to regain the memoried shape in an austenitic state when warmed to a selected temperature, above the temperature transformation level, such as human body temperature. The two interchangeable shapes are possible because of the two distinct microcrystalline structures that are interchangeable with a small variation in temperature. The temperature at which the device assumes its first configuration may be varied within wide limits by changing the composition of the alloy. Thus, while for human use the alloy may be focused on a transition temperature range close to 98.6° F., the alloy readily may be modified for use in animals with different body temperatures.

U.S. Pat. No. 4,425,908 to Simon discloses a blood clot filter formed of thermal shape memory material while U.S. Pat. Nos. 3,868,956 to Alfidi et al., 4,503,569 to Dotter, 4,512,338 to Balko et al., 5,354,308 and 5,395,390 to Simon et al. and European Application No. 0556,850A1 disclose stents of thermal shape memory material. Although these patented units operate effectively, it becomes necessary to provide devices in a large number of sizes to accommodate vessels of different sizes or to vary the contact pressure between an expanded device and a vessel wall. With such prior units, when segments of different lengths expand into contact with a vessel wall, it has not been possible to achieve a substantially uniform contact pressure for all such segments. Longer segments tend to contact the wall with a greater contact pressure than the shorter segments.

SUMMARY OF THE INVENTION

It is a primary object of the present invention to provide a vessel implantable appliance of shape memory material having temperature induced austenitic and martensite states with a hinged joint subject to stress induced martensite phase transformation.

Another object of the present invention is to provide a novel and improved vessel implantable appliance of shape memory material wherein strain and flexion in the material are localized at a hinged joint. The shape memory material has a low temperature martensite state where the material is flexible and a high temperature austenitic state where the material returns to a predetermined state and becomes relatively rigid. When the material is in the austenitic state, stress induced martensite can occur, and the hinged joint is designed so that stress induced martensite occurs at the joint.

A further object of the present invention is to provide a novel and improved vessel implantable appliance of shape memory material wherein strain and flexion in the material are localized at a hinged joint. By having the joint subject to stress induced martensite phase transformation, and by locating the joint in sections of the appliance which expand into contact with a vessel wall during a temperature induced austenitic phase, the appliance section will exert a substantially constant force on the vessel wall over a large range of deflections. Also the potential for fatigue fractures of the material due to cyclic respiratory, cardiovascular or postural motions is reduced.

A still further object of the present invention is to provide vena cava filters and stents of Nitinol which operate in a temperature induced austenitic state to exert a constant force on the walls of a vessel regardless of variations in vessel cross-sectional area or variations in the length of sections of the devices which contact the vessel walls.

DETAILED DESCRIPTION

By forming the body of a medical device of a Nitinol alloy material, such as Nitinol wire, transition between the martensitic and austenitic states of the material can be achieved by temperature transitions above and below a transition temperature or transition temperature range. Such controlled temperature transitions have conventionally been employed to soften and contract the Nitinol body for a medical unit to facilitate insertion into a catheter and to subsequently expand and rigidify the body within a vascular or other passageway. In addition to temperature sensitivity, it has been found that Nitinol, when in the temperature induced austenitic state, is also subject to stress sensitivity which can cause the material to undergo a phase transformation from the austenitic state to the martensitic state while the temperature of the material remains above the transition temperature level. When sufficient stress is applied to a Nitinol strand in the austenitic state to initiate a phase transition to the martensitic state, the material reaches a superelastic plateau which extends over approximately a 2% to 7½% stress range. When the material in the martensitic state reaches the superelastic plateau, additional applied stress within the plateau range is taken up by the phase transformation. This superelastic plateau can be utilized in the design of a Nitinol medical unit which will apply a substantially equal pressure to the walls of a body passageway regardless of variations in the length of segments of the unit which contact such walls. Also, a Nitinol medical unit of a single size can be used in body passageways of different diameters or cross-sectional areas while still applying a substantially equal pressure to the walls of these variously sized passageways.

Figure 1:
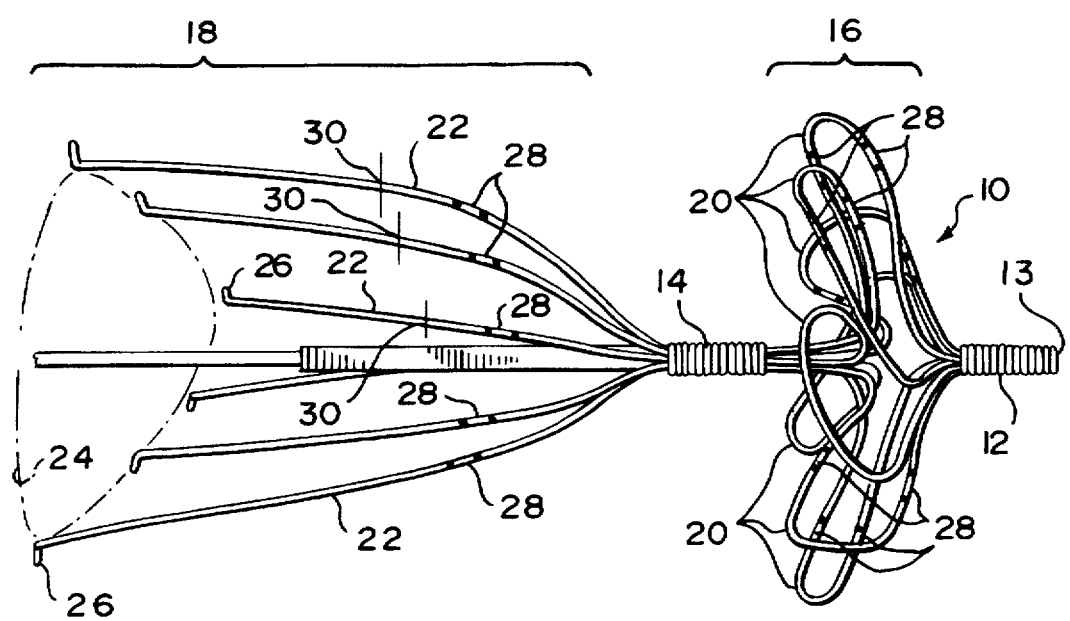
FIG. 1 is a side view of a vena cava filter formed with superelastic hinged joints.
Figure 2:
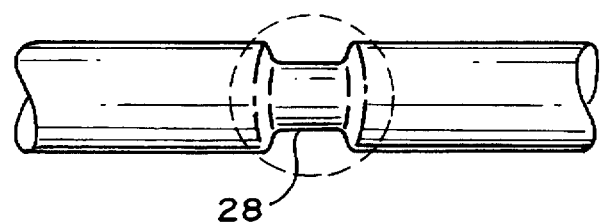
FIG. 2 is an enlarged view of the superelastic hinged joint of FIG. 1.
Figure 3:
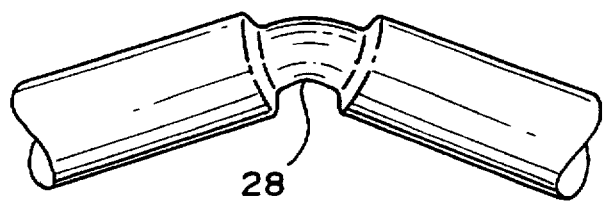
FIG. 3 is an enlarged view of the superelastic hinged joint of FIG. 2 in a flexed configuration.

Referring now to FIGS. 1, 2 and 3, a blood clot filter 10 is illustrated which is made from a set of Nitinol wires. The wires are held together by two small sleeves or coils 12 and 14 of the same material, each coil being spot welded to hold it in place and approximately one-quarter of an inch in length. Coil 12 is adjacent the tip 13 of the wires, and coil 14 is approximately two inches from tip 13 when the wires are fully extended. In the low temperature martensite phase of the material, the set of wires can be straightened and held in a straight form that can pass through a length of fine plastic tubing with an internal diameter of approximately 2 mm (#8 French catheter). In its high temperature austenitic form, the filter 10 recovers a preformed filtering shape.

In its normal expanded configuration or preformed filtering shape, filter 10 is a double filter, having a first filter basket 16 and a second filter basket 18. The two filter baskets provide peripheral portions which engage the inner wall of the vein at two longitudinally spaced locations. The two filter baskets are generally symmetrical about a longitudinal axis passing through filter tip 13.

The mesh of first filter basket 16 is formed from the sections of wires between the two quarter-inch coils 12 and 14. The mesh is made up a series of seven overlapping loops 20 arranged to form a rosette approximately 25 mm in diameter. The loops are angled slightly relative to the longitudinal axis of filter 10 and this angle can be varied to accommodate somewhat smaller diameters if the device is to be constrained in a tube of less than 25 mm in caliber. The loops 20 effectively divide the cross-sectional area to be filtered. The rosette formed by loops 20 can expand or be compressed to fit various sizes of vein. The peripheral portions or tips of the loops 20 press outwardly against the inner wall of the vein, although without becoming imbedded in the vein; loops 20 thereby help to keep filter 10 in place. First filter basket 16 is convex relative to filter tip 13.

The mesh of second filter basket 18 is formed by the six circumferentially spaced free wire ends or legs 22, which tilt and bow outwardly of the longitudinal axis of filter 10. The six free ends or legs 22 that extend beyond the second quarter inch coil 14 diverge so that their tips form a circle 24 at their maximum divergence. Each leg is also bowed outwardly slightly. The legs serve to orient the device relative to the longitudinal axis of the vena cava. Second filter basket 18 is convex relative to filter tip 13.

Each free end of a leg 22 is bent sharply outward at about a right angle to form a hook 26 of approximately 1.5 mm in length. The hooks are intended to engage the wall of the vena cava to prevent migration proximally or distally. The six legs 22 are of slightly different lengths to permit good packing within the delivery device. If legs 22 are all of a single length, the hooks may interfere with one another, so that the filter does not expand properly when delivered into the vein.

The variable lengths of the legs 22 can result in each leg engaging the wall of the vena cava with a different contact pressure when the filter 10 is subjected to a temperature at or above the transition temperature. This is often undesirable, and to eliminate this variation in contact pressure a superelastic hinged joint 28 is provided in each of the legs 22. The hinged joint 28 is formed by reducing the cross-sectional area of the Nitinol wire forming a leg or other portion of the filter in a small localized area as illustrated in FIGS. 2 and 3 to localize stress deformation at the hinged joint. The cross-section of the hinged joint may be circular, rectangular, ovoid or some other desirable shape and the transition from the full wire cross-section to the reduced hinged joint cross section may be abrupt, tapered, rounded, or any combination of these. The force to be exerted by the legs 22 on the vessel wall is now determined primarily by the geometry of the hinged joint 28 and modern machining techniques allow this geometry to be precisely controlled.

Figure 4:
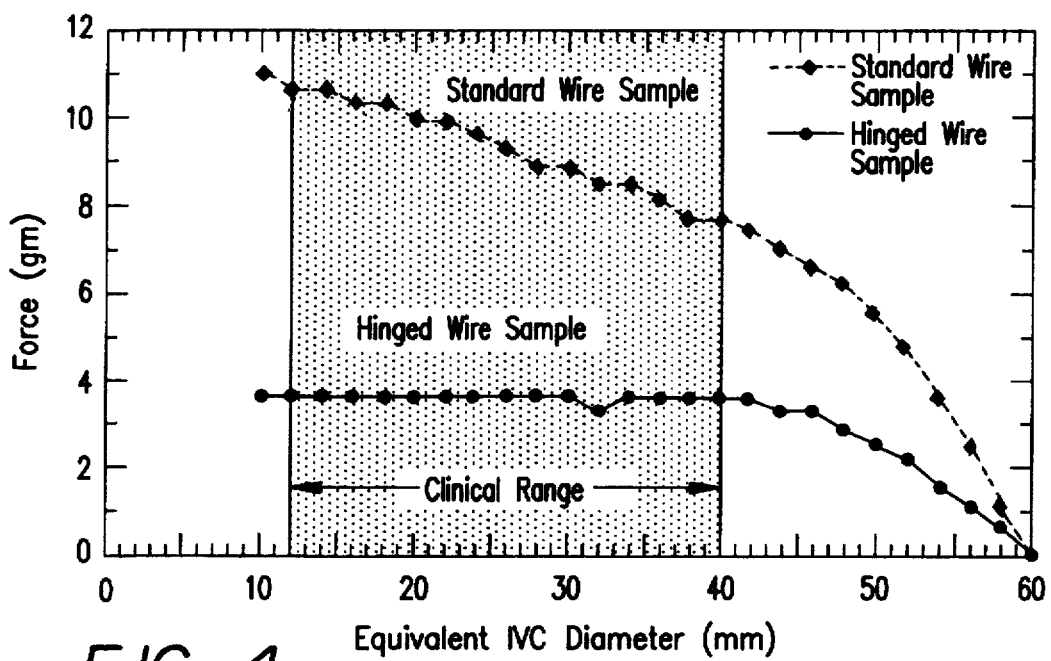
FIG. 4 is a chart showing the forces on a vessel wall exerted by standard appliances of Nitinol and the appliances of the present invention.

In the legs 22 of the filter 10, the hinged joints 28 should be of substantially the same cross-sectional geometry and located as shown between the coil 14 and the halfway point 30 along the length of each leg. As will be noted in FIG. 1, the maximum inclination of each leg relative to the central longitudinal axis of the filter 10 occurs in this first half of the leg adjacent to the coil 14, and this area is subjected to greater stress as the leg expands and contacts the passageway wall. By localizing stress deformation and flexion in the wire at a hinged joint 28 located in this first half of the leg, sufficient stress is applied so that the Nitinol wire at the hinged joint undergoes a phase transformation from the austenitic state to the martensitic state and reaches the superelastic plateau. As the hinged joints 28 experience stress variations within the range encompassed by the superelastic plateau, they flex as shown in FIG. 3 and cause the legs 22 to provide a substantially uniform contact pressure against the passageway wall. Thus if the hinged joint 28 in each leg 22 is formed to have substantially the same cross-sectional area, each leg will engage the wall of the vena cava with substantially the same contact pressure regardless of the variations in leg length and deflection. This is illustrated by the chart of FIG. 4 which shows the contact pressure curve for legs without the hinged joint 28 versus the curve for legs with the hinged joint. Since the hinged joint is in the stress induced martensitic state while the remainder of the leg is in the austenitic state, flexure at the joint not only causes the leg to exert a constant force over a range of deflections, but also reduces the potential for fatigue fractures of the filter legs due to cyclic respiratory, cardiovascular or postural motions.

To quantify the effect of adding a superelastic hinged joint to the filter leg, in-vitro force measurements were conducted on lengths of Nitinol wire with and without hinged joints. The wires were maintained at 37° C. in a water bath and were deflected through distances that are anatomically relevant. These deflections were correlated to equivalent caval diameters. Unhinged filter wire samples exerted forces that depend on deflection (see upper curve of FIG. 4). In this experiment, the force ranged between 7.5 and 10.5 gm over the expected range of vena cava sizes between 12 and 36 mm diameter. In contrast, hinged joint wire samples exerted a force that was insensitive to deflection (lower curve of FIG. 4), in this instance at a value of 3.5 gm. The force level is determined by the diameter of the joint segments, the length of the segments, and their displacement from the pivot point.

In the past, Nitinol filters, stents, and other medical devices designed for expansion into contact with the wall of a vascular or other body passageway had to be sized to conform to the cross-sectional area of the passageway, for a device which was significantly larger than the passageway would exert excessive contact pressure on the walls thereof. To prevent this, each device had to be manufactured in a large number of sizes. By forming Nitinol medical devices with the superelastic hinged joint 28 in accordance with the present invention, a reduced number of device sizes are required. By placing a hinged joint or joints on each segment of the medical device which contacts the wall of a passageway, a single device can be used for passageways of varying cross-sectional areas. The increased stress on a segment resulting from contact with a smaller passageway would be localized at the hinged joint 28 and the hinged joint would cause the segment to engage the walls of the smaller passageway with substantially the same contact pressure that would be applied to the walls of a larger passageway. Thus a single device could be effectively used with passageways of different cross-sectional areas so long as the stress range for the superelastic plateau of the hinged joint is not exceeded.

In FIG. 1, superelastic hinged joints 28 were formed in the legs 22 of the filter 10. These hinged joints could also be provided as shown in the Nitinol wire on opposite sides of each loop 20, as these loops also engage the walls of a vein.

Figure 5:
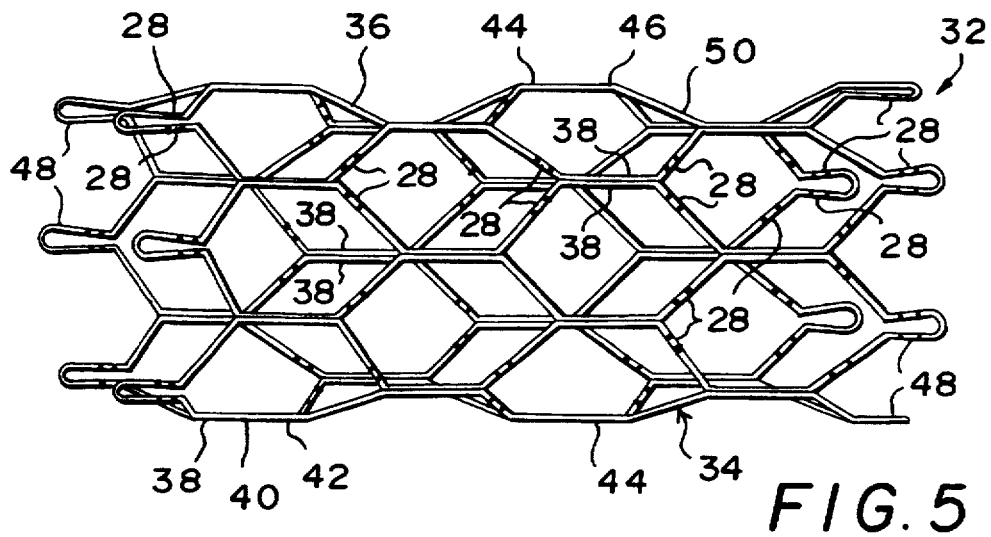
FIG. 5 is a perspective view of a stent with the superelastic hinged joints of the present invention.
Figure 6:
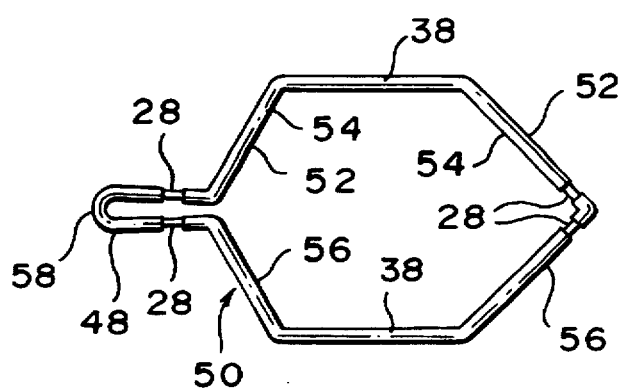
FIG. 6 is a view of a cell of the stent of FIG. 5 with superelastic hinged joints.

The superelastic hinged joints 28 may be effective when formed in the expandable section of any Nitinol medical device. For example, FIGS. 5 and 6 illustrate a stent 32 which includes a skeletal frame 34, preferably formed from a single Nitinol wire 36. The wire includes a plurality of abutting straight portions 38 which are joined to each other, as by welding or by other attachment means. When the frame 34 is expanded in the austenitic state, it becomes relatively rigid, and substantially tubular in configuration. Ends 40, 42 of the single wire 36 are disposed in one of the straight portions 38, such that there are no exposed wire free ends, disposed within or extending from the frame 34. The abutting and elongated straight portions of the wire facilitate the use of strong elongated welds to securely join the wire portions together. The wire 36 may be formed of any desired cross-sectional shape. In the frame, straight portions 38 of the joined wire segments are disposed, relative to the tubular configuration of the frame, circumferentially thereof. The wire abuts itself only at the straight portions 38 and does not cross itself at any point. Accordingly, the frame walls, that is, walls 44 of a tubular body portion 46 of the frame have a thickness equal to the diameter of the wire 36.

The stent includes the body portion 46 and looped finger portions 48 extending generally axially from one, or both, ends of the body portion. The finger portions also expand radially outwardly against the wall of a vascular passageway in which the stent is located.

The tubular body portion 46 comprises a mesh formed by the wire 36, the mesh comprising a plurality of interconnected cells 50 which are preferably of a polygonal configuration when viewed in plan, providing spaced, substantially parallel straight sides to form the aforementioned straight portions 38. The cells 50, when polygonal, are preferably of a hexagonal configuration, which readily provides expansion and rigidity characteristics desirable in the structure and operation of the device. Preferably, the stent comprises six of the polygonal cells 50 circumferentially and an even number of the polygonal cells along its length, thereby facilitating formation of the stent by the single wire 36.

It is important to note that each cell 50 is formed by two straight portions 38 which are substantially parallel to the central longitudinal axis of the stent or stent section of which the cell is a part. Each end of the cell is closed by an end wall or end walls 52 which extend between adjacent ends of the straight portions; the end walls being disposed at an angle to the central longitudinal axis of the stent or stent section containing the cell. It is these end walls which expand and contract as the cell undergoes a phase transformation between the austenitic and martensitic states. The straight portions 38 remain parallel to the central longitudinal axis of the stent as the stent expands or collapses.

The cell structure and orientation within the stent 32 is very important to the proper expansion and compression characteristics of the stent. Since cell joinder is accomplished solely at adjoining straight portions 38, the expansion of the stent radially and outwardly from the central longitudinal axis thereof places minimal stress on the connections between cells. The straight portions 38, being parallel to the longitudinal axis of the stent or stent section, do not significantly change in configuration as the stent is collapsed and expanded.

Since the sole connection between cells is along these straight portions, the connection is not subjected to tension or shear force during expansion and compression of the stent in a manner which would tend to stress and break the connection. The end walls 52, which are inclined relative to the central longitudinal axis of the stent or stent section, are the portions of the cell which provide the radial memory force during expansion, and the longitudinally oriented connections between the cells causes the cells to distribute this radial memory force evenly around the stent. It is the pliability of the end walls at temperatures below the temperature transformation level which cause the cell straight portions 38 to move together as the stent is compressed, and it is these same end walls which become relatively rigid but resiliently deformable to return the stent to its thermal memory shape at temperatures above the temperature transformation level. As these end walls maintain the straight portions 38 of the cells substantially parallel to the longitudinal axis of the stent in all configurations of the stent, these straight portions are not significantly biased or stressed.

To adapt a stent 32 of a single size for use in vessels of different cross-sectional areas, the expandable portions of the stent, like those of the blood clot filter 10, are provided with superelastic hinged joints 28. As shown in FIGS. 5 and 6, a hinged joint 28 can be formed at the apex between the wall sections 54 and 56 of each end wall 52 where maximum stress occurs. Alternatively, a hinged joint 28 can be formed in each wall section 54 and 56 in closely spaced relationship to the apex therebetween. Also, a hinged joint 28 can be formed in the Nitinol wires on either side of the end loop 58 for each of the fingers 48.

I claim:

1. A medical appliance of shape memory material for implantation in a vessel for engagement with walls of the vessel comprising:

a body formed of thermal shape memory material having a temperature transformation level below which said material is in a martensitic state and said body is relatively pliable and compressible and above which said material is in an austenitic state and said body is self-expandable to a substantially rigid, precompressed configuration, said shape memory material in the austenitic state being capable of transformation to the martensitic state in response to induced stress, said body having a longitudinal axis and including segments which expand outwardly away from said longitudinal axis when said thermal shape memory material is in a thermally induced austenitic state, and at least one superelastic hinged joint formed in at least one of such segments to localize strain to which said segment is subjected at said joint, to permit said joint to undergo a stress induced phase transformation to a martensitic state while the remainder of said segment is in a temperature induced austenitic state, said joint being formed by reducing the cross-sectional area of said segment in a localized area of said segment.

2. The medical appliance of claim 1 wherein said shape memory material is Nitinol.

3. The medical appliance of claim 2 wherein said segment includes an elongate section of Nitinol wire, said superelastic joint being formed by reducing the cross-sectional area of said wire to cause strain at said joint when the wire is in the temperature induced austenitic state to induce a transformation of said joint to the stress induced martensitic state while the remainder of the wire remains in the austenitic state.

4. The medical appliance of claim 3 wherein the temperature transformation level of said wire is about body temperature.

5. The medical appliance of claim 2 which comprises a blood clot filter having a body including a plurality of wire portions, said filter having a leading end located on said longitudinal axis, said wire portions being confined together at said filter leading end to form a tip, and being confined together at a median place on said axis spaced from said filter leading end, said wire portions having free ends remote from said tip and said median place, said wire portions between said median place and said free ends defining legs, and a superelastic joint formed in each such leg between the median place and free end thereof.

6. The medical appliance of claim 5 wherein said superelastic joint is formed in each such leg between said median place and a point halfway between said median place and the free end of said leg.

7. The medical appliance of claim 6 wherein said legs in the austenitic state of said Nitinol wire bow outwardly from said median place and include a foot extending at an angle at the free end of each said leg.

8. The medical appliance of claim 6 wherein each wire portion between said filter tip and said median place forms a loop, said loops overlapping at least the adjacent two said loops to form a filter basket.

9. The medical appliance of claim 8 wherein each such wire portion forming said loop includes a first wire section extending outwardly from said median place a second wire section extending outwardly from said filter tip and a curved section extending between said first and second wire sections to form the end of said loop, a superelastic joint being formed in each said first, and second wire sections spaced from said curved section.

10. The medical appliance of claim 6 wherein said filter includes coaxial first and second filter baskets, each said filter basket being generally symmetrical about said longitudinal axis and opening away from said filter leading end.

11. The medical appliance of claim 2 which comprises a stent including an elongate body member having a longitudinal axis with a skeletal frame of said wire formed to define an elongate chamber which extends through said body member, the skeletal frame being formed to assume a first expanded configuration relative to said longitudinal axis in the austenitic state of said wire and to be collapsible toward said longitudinal axis to a second collapsed configuration in the martensitic state of said wire, said skeletal frame further being formed to define a plurality of interconnected open cells with each of said cells including two substantially parallel, spaced side walls which are substantially parallel to said longitudinal axis in both the first expanded configuration and the second collapsed configuration of said skeletal frame and end walls extending between said sidewalls at an angle to said longitudinal axis, and a superelastic joint formed in each of said end walls, said cells being arranged around said elongate chamber with sidewalls of adjacent cells arranged in adjacent coextensive relationship, said cells joined together by an attachment connecting adjacent, coextensive cell sidewalls, this being the only connection between said cells.

12. The medical appliance of claim 11 wherein said cell end walls each include first and second wall sections, each said wall section having a first end joined to one of the sidewalls of said cell, said wall section extending at an angle to the sidewall to which the first end thereof is joined, and each said wall section having a second end opposite to said first end, the second ends of said first and second wall sections being joined, each said wall section having a superelastic joint formed therein.

13. The medical appliance of claim 12 wherein said superelastic joint in each of said first and second wall sections is located adjacent the second ends thereof.

14. The medical appliance of claim 11 wherein said wire forming said skeletal frame is configured to form finger portions extending axially from an end of said body member, each said finger portion including at least one superelastic joint formed therein.

15. The medical appliance of claim 12 wherein each such finger portion is configured in the form of a loop having first and second spaced wire sections extending axially from an end of said body and a curved section extending between said first and second wire sections to form an outermost end of said loop, a superelastic joint being formed in each said first and second wire sections spaced from said curved section.

16. The medical appliance of claim 2 which comprises a stent including a wire skeletal frame of generally tubular configuration, said skeletal frame comprising only a single wire, said frame including straight axially-extending portions of said wire joined together along the lengths of said straight axially-extending portions, and disposed side by side defining a circumference of said stent, wherein said frame includes a substantially tubular body portion and finger portions extending from an end of said body portion, said finger portions extending axially of said body portion and comprising endless looped portions of said single wire, each such finger portion including first and second spaced wire sections extending axially from an end of said body portion and a curved section extending between said first and second wire sections to form an outermost end of said finger portion, a superelastic joint being formed in each said first and second wire sections spaced from said curved section.

* * * * *